United States Patent
Nichols et al.

(10) Patent No.: US 10,520,447 B2
(45) Date of Patent: Dec. 31, 2019

(54) PAINT INSPECTION LIGHTING SYSTEM

(71) Applicant: AVID Labs, LLC, Fort Wayne, IN (US)

(72) Inventors: Joel A. Nichols, Columbia City, IN (US); Alexander W. Tollington, Fort Wayne, IN (US); Benjamin R. Powers, Fort Wayne, IN (US); Michael H. Kretschmer, Fort Wayne, IN (US)

(73) Assignee: Avid Labs, LLC, Fort Wayne, IN (US)

( * ) Notice: Subject to any disclaimer, the term of this patent is extended or adjusted under 35 U.S.C. 154(b) by 301 days.

(21) Appl. No.: 15/460,929

(22) Filed: Mar. 16, 2017

(65) Prior Publication Data

US 2017/0268985 A1  Sep. 21, 2017

Related U.S. Application Data

(60) Provisional application No. 62/310,294, filed on Mar. 18, 2016.

(51) Int. Cl.
*G01N 21/88* (2006.01)

(52) U.S. Cl.
CPC ... *G01N 21/8803* (2013.01); *G01N 2201/062* (2013.01)

(58) Field of Classification Search
CPC .............. F21V 17/06; G01N 2021/062; G01N 2021/8816; G01N 21/8806; G01N 2201/062
See application file for complete search history.

(56) References Cited

U.S. PATENT DOCUMENTS

| | | | |
|---|---|---|---|
| 4,114,327 A | 9/1978 | Williams | |
| 5,636,024 A | 6/1997 | Cookham et al. | |
| 5,853,215 A | 12/1998 | Lowery | |
| 5,870,872 A * | 2/1999 | Hinnen | E04F 21/1811 182/141 |
| 5,911,500 A * | 6/1999 | Barnett | G01N 21/8806 362/145 |
| 6,462,813 B1 | 10/2002 | Haven et al. | |
| 6,532,066 B1 | 3/2003 | Filev et al. | |
| 6,843,599 B2 | 1/2005 | Le et al. | |
| 7,486,768 B2 | 2/2009 | Allman et al. | |
| 2003/0010576 A1 | 1/2003 | Malone, Jr. | |
| 2012/0002406 A1 * | 1/2012 | Leadford | F21S 2/005 362/217.14 |

(Continued)

FOREIGN PATENT DOCUMENTS

| | | |
|---|---|---|
| CN | 202827285 U | 3/2013 |
| DE | 195 34 145 A1 | 4/1996 |

(Continued)

*Primary Examiner* — Robert J May
*Assistant Examiner* — Leah Simone Macchiarolo
(74) *Attorney, Agent, or Firm* — Taylor IP, P.C.

(57) ABSTRACT

An inspection lighting system including a first frame structure and a plurality of linear light arrays coupled to the first frame structure. Each of the linear light arrays have a plurality of integrated lights and at least one generally linear bracket. The integrated lights are arranged end-to-end, with each of the integrated lights having at least one T-slot along at least a portion of a length of the integrated light. The linear bracket coupling adjacent ones of the integrated lights together using the T-slots in the adjacent integrated lights.

20 Claims, 4 Drawing Sheets

(56) References Cited

U.S. PATENT DOCUMENTS

| | | | |
|---|---|---|---|
| 2013/0057678 A1* | 3/2013 | Prior Carrillo | G01N 21/8806 348/125 |
| 2013/0094225 A1* | 4/2013 | Leichner | F21S 2/005 362/368 |
| 2016/0097725 A1* | 4/2016 | Porter | G01N 21/8803 356/237.2 |
| 2017/0146226 A1* | 5/2017 | Storey | F21V 29/56 |

FOREIGN PATENT DOCUMENTS

| | | |
|---|---|---|
| DE | 195 19 777 A1 | 12/1996 |
| DE | 198 20 536 C1 | 10/1999 |
| DE | 101 10 994 A1 | 3/2002 |
| EP | 1 006 349 A1 | 6/2000 |
| JP | 2007-278713 | 10/2007 |
| JP | 4084150 B2 | 2/2008 |

* cited by examiner

PAINT INSPECTION LIGHTING SYSTEM

CROSS REFERENCE TO RELATED APPLICATIONS

This is a non-provisional application based upon U.S. provisional patent application Ser. No. 62/310,294, entitled "RAPID DEPLOYMENT SYSTEM FOR PAINT INSPECTION BOOTHS", filed Mar. 18, 2016, which is incorporated herein by reference.

BACKGROUND OF THE INVENTION

1. Field of the Invention

The present invention relates to a lighting system that can be rapidly deployed for use, for example, as inspection lighting for the inspection of paint.

2. Description of the Related Art

Traditionally fluorescent linear lighting systems have been used in auto plants. These systems are becoming increasingly outdated with the introduction of LED technology. The current systems and new LED replacement systems have several flaws that the present invention overcomes.

A linear array of lights is used (also called Zebra lighting) at designated spacings between the lights, which is often 12 inches apart but this can vary. The inspection staff view the reflection of the line of light at different angles to observe defects, the optimum angle is normally 30 degrees however this will vary depending upon the shape of the painted surface, which can be the painted body of a vehicle that is being inspected.

Flaw One—With the prior art systems is that there is a gap present between the linear tubes thus creating an area that could miss paint defects due to the lack of reflected lights in these areas.

Flaw Two—is that the prior art systems have a low life span prior to replacement when compared to LED products with life spans in excess of 5 years.

Flaw Three—is that the prior art replacement systems are laborious to install and have no means of rapid deployment thus limiting the installation deployment during a paint line retrofit.

Flaw Four—prior art systems use separate frames and ancillary support structures to erect a replacement or new paint inspection booth. This leads to excessive material usage during construction and additional components.

Flaw Five—prior art systems use fluorescence light sources that are "spiky" in their emitted light spectrum, this leads to fatigue of staff and missed defects.

What is needed in the art is a quickly erectable inspection light system that can be manufactured in an economic manner.

SUMMARY OF THE INVENTION

Embodiments of the present invention are for an inspection lighting system, which is for the inspection of paint applied to vehicles.

The invention in one form is directed to an inspection lighting system including a first frame structure and a plurality of linear light arrays coupled to the first frame structure. Each of the linear light arrays have a plurality of integrated lights and at least one generally linear bracket. The integrated lights are arranged end-to-end, with each of the integrated lights having at least one T-slot along at least a portion of a length of the integrated light. The linear bracket coupling adjacent ones of the integrated lights together using the T-slots in the adjacent integrated lights.

The invention in another form is directed to an inspection lighting system a first frame structure, and a plurality of linear light arrays coupled to the first frame structure. Each of the linear light arrays has a plurality of integrated lights with adjacent ones of the plurality of integrated lights being coupled end-to-end defining a joint; and at least one light emitter coupled at the joint. The light emitter covers a non-light emitting portion of each of the adjacent integrated lights.

Advantageously, the present invention provides a rapidly deployable paint inspection system having integrated lights that have structural properties that allow them to be coupled end-to-end.

Additional features and advantages of the invention will be made apparent from the following detailed description of illustrative embodiments that proceeds with reference to the accompanying drawings.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
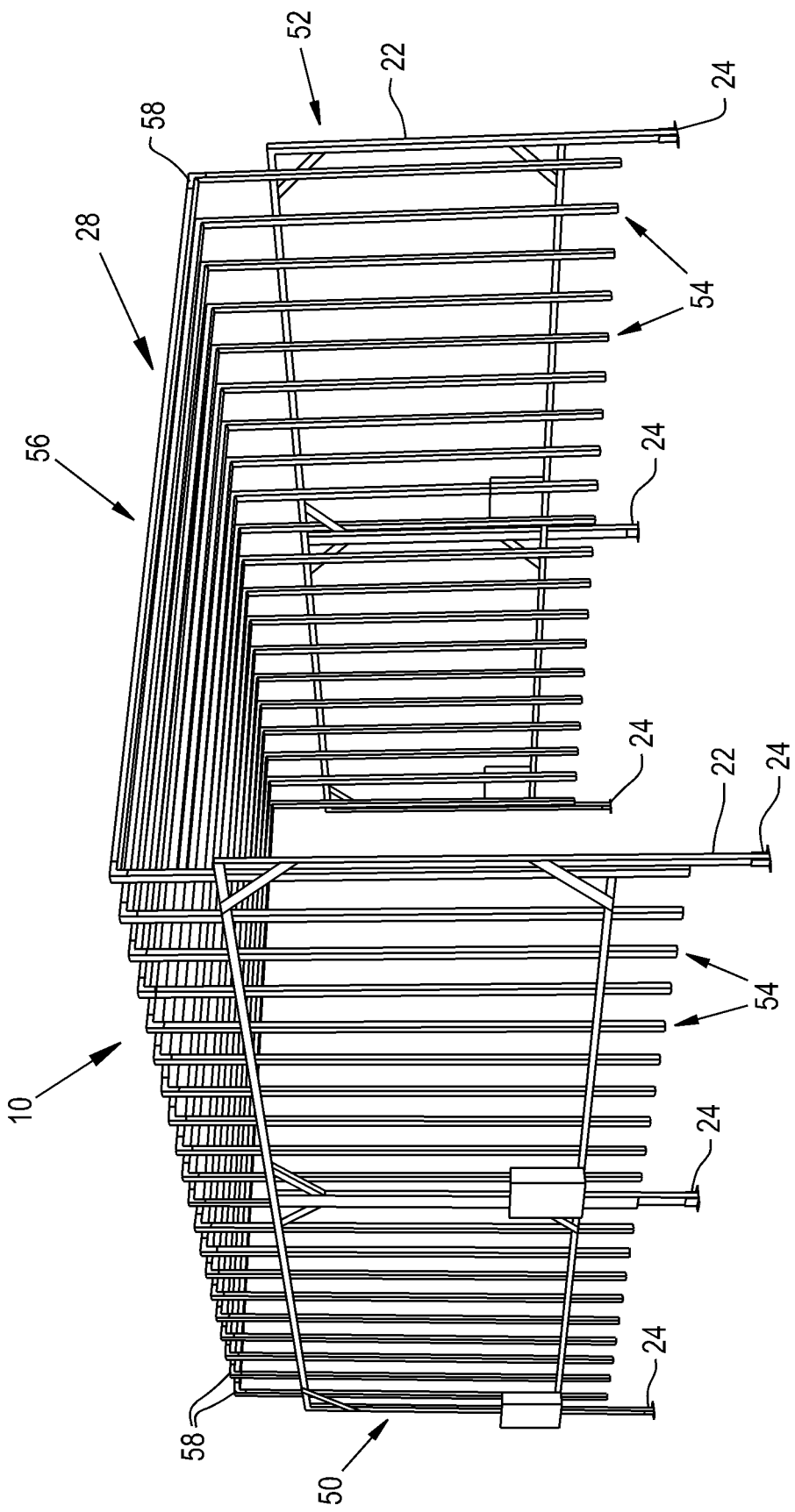
FIG. 1 is a perspective view illustrating an inspection lighting system of the present invention.

Referring now to the drawings, and more particularly to FIGS. 1-7, there is illustrated an embodiment of a system for erecting a paint booth inspection lighting apparatus 10, of the present invention. Inspection lighting system 10 includes frame structures 50 and 52 to which are attached a plurality of linear light arrays 54 in a generally vertical manner with similar linear light arrays 56 arranged generally horizontally overhead, and which are attached at each end to corresponding ends of linear light arrays 54. Each linear light array 54 and 56 include a plurality of individual integrated lights 16 arranged end-to-end, each of the integrated lights 16 having at least one T-slot 12 along at least a portion of a length of the integrated light 16.

There is at least one generally linear bracket 18 coupling adjacent integrated lights 16 together using the T-slots 12 in the adjacent integrated lights 16. Bracket 18 only couples adjacent integrated lights together and is not coupled to frame 50 or 52.

Frame structures 50 and 52 are arranged so that they are substantially parallel to each other. The linear light arrays 54 that are coupled to frame structures 50 and 52 are arranged so that they generally emanate light toward the opposite frame structure 50 or 52. Each linear light array 54 has an angular bracket 58 coupled to an end thereof, with bracket 58 also coupled to an end of linear light array 56, with the opposite end of each linear light array 56 being coupled to a linear light array on the opposite frame structure by way of another bracket 58. The angular brackets 58 uses the T-shaped slots of the integrated lights 16 by way of fasteners 30 to effect the construct.

The linear light arrays 56 are only coupled to the linear light arrays 54 and are not directly connected to either frame 50 or 52. Another way of stating this arrangement is that the top linear light arrays 56 are coupled to linear light arrays 54 coupled to frame structure 50 and they are also coupled to linear light arrays 54 coupled to frame structure 52.

Paint inspection lighting system 10 can, for example, be used in an automotive plant, with the lighting system 10 allowing for a reduced erection time to thereby reduce labor install time thus providing decreased down time when retrofitting paint inspection lines.

Figure 2:
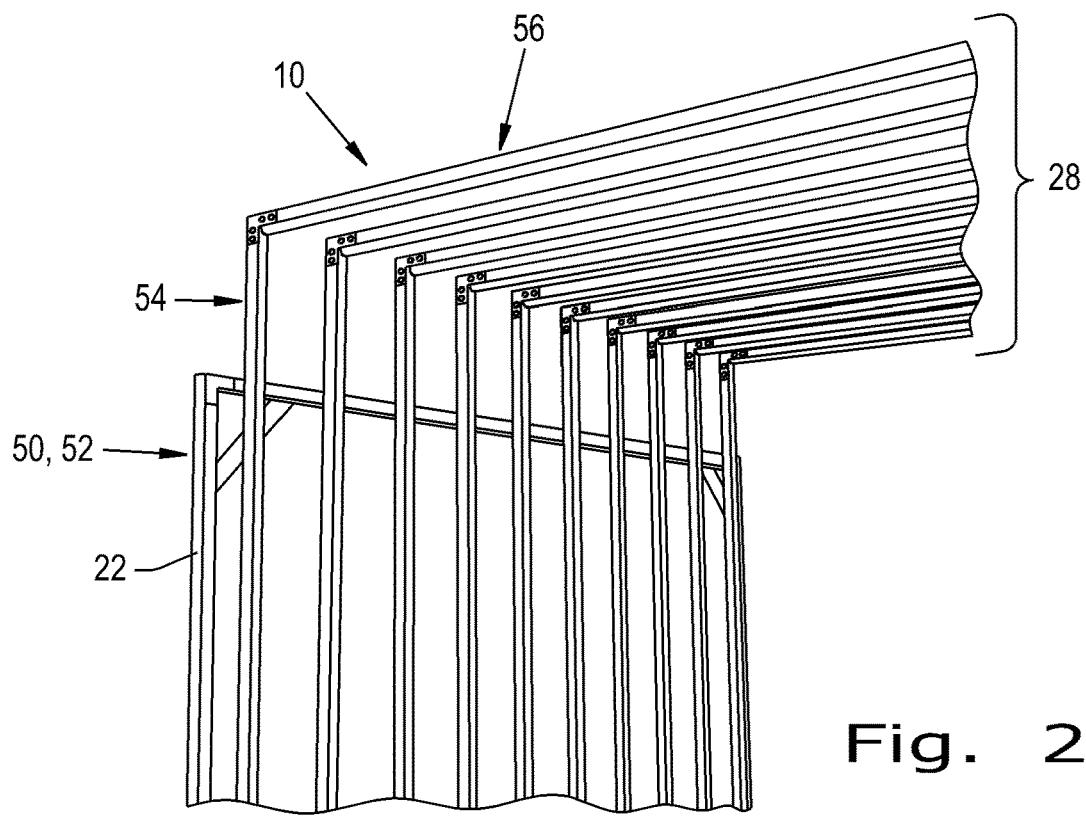
FIG. 2 is a perspective view illustrating some of the linear light arrays used in the lighting system of FIG. 1.
Figure 3:
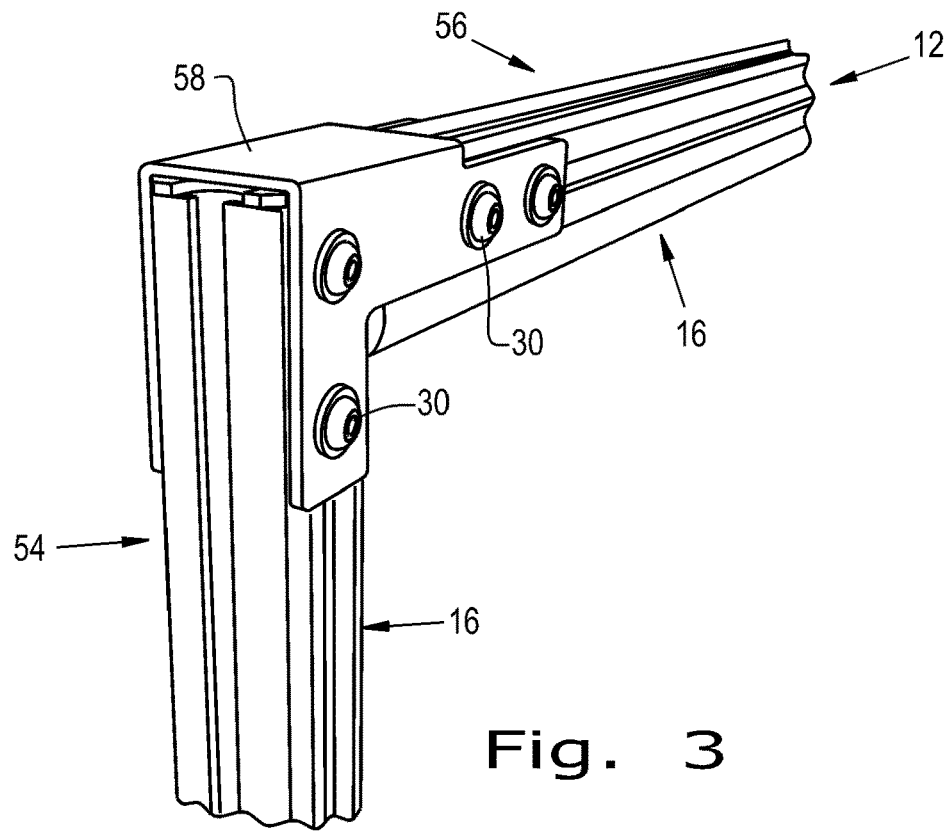
FIG. 3 is a perspective view showing the use of an angled bracket that couples the top linear light array to a side linear light array of the lighting system of FIG. 1.
Figure 4:
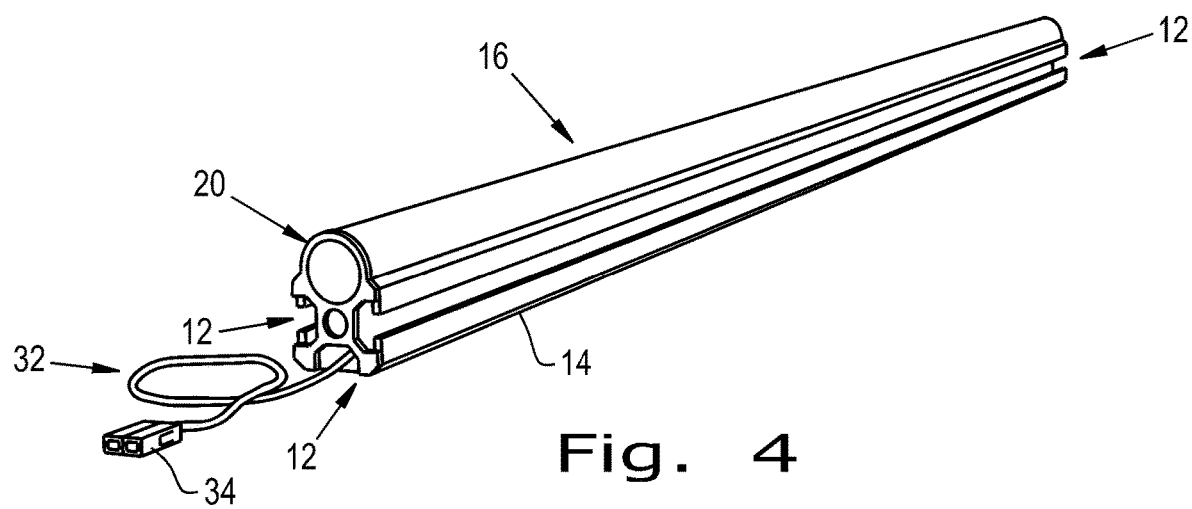
FIG. 4 is a perspective view illustrating a configuration of an integrated light used in the light arrays of FIGS. 1-3.
Figure 5:
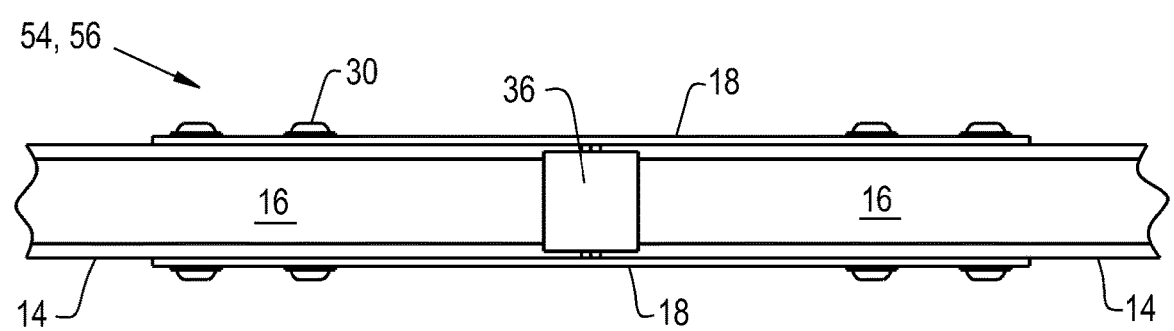
FIG. 5 illustrates the end-to-end coupling of the integrated lights of FIGS. 1-4.
Figure 6:
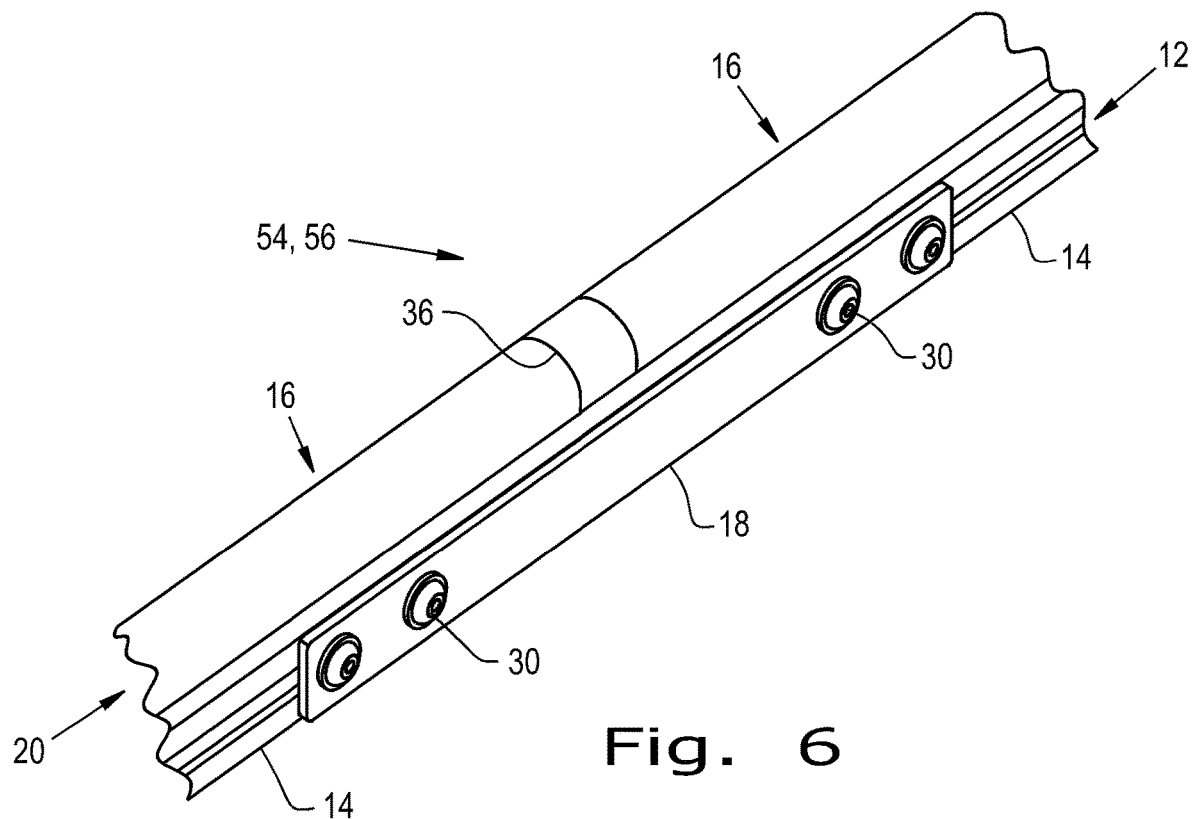
FIG. 6 is a perspective view of the coupled integrated lights of FIG. 5.
Figure 7:
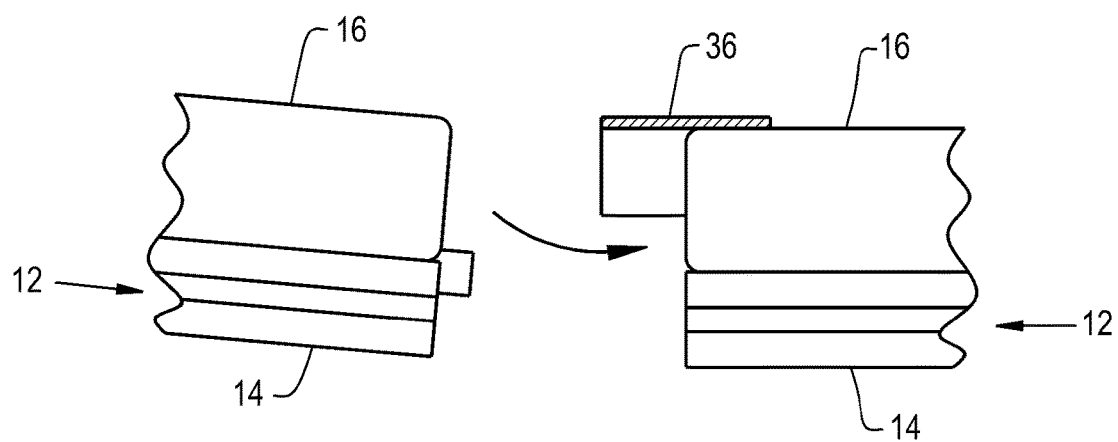
FIG. 7 illustrates the coupling of two adjacent integrated lights.

Lighting system 10 takes advantage of the T slots 12 located in three positions at 90, 180 and 270 degrees on a linear extrusion 14 of lighting component 16 allowing for linkage between brackets 18 or 58. The extrusion 14 encompasses LEDs 20 (Light Emitting Diodes) on the 0 degree face of extrusion 14 thus light and structural elements are combined. The linkage of T slots 12 between extrusions allows for pre-assembled frames 22 to be constructed away from the paint inspection area prior to the planned install. Pre-assembled frames 22 include a frame structure 50 or 52 along with spaced apart linear light arrays 54 coupled thereto. As can be seen in FIGS. 1 and 2 a portion of the frame structure 22 is generally perpendicular to the linear light arrays, and that the linear light arrays 54, 56 are generally parallel to each other.

During install a pre-assembled side panel 22 is carried into the paint area and bolted to the floor or ground in the specified location. Feet 24 are pre-attached to the panel section at set distance to allow for easy quick deployment and minimal ground bolting. A second section 22 is deployed on the opposite side at set distance and in the same manner. Overhead preassembled sections 28 with right angled joints 58 (or 45 degree joints, depending upon booth type) are then lifted into position. Tightening bolts are fastened at each position. The process is repeated along the production line until the desired replacement length is achieved.

Quick connect power feeds 32 and connectors 34 are located on the back of each linear LED light 16 for rapid coupling to the power supply in to the paint booth sections, this removes on site wiring simplifying the system. A light transmitting end cap 36 is positioned on the end of each light 16 where there is an adjacent light 16 allowing for a continuous light source when joining lighting components 16 together. End cap 36 can also be thought of as a light emitter 36 coupled at the joint, with the light emitter 36 covering a non-light emitting portion of each of the adjacent integrated lights 16. Light emitter 36 may be passive in that it receives light energy from a portion of the LEDs 20 and then channels the light energy so that it is transmitted outward over the non-light emitting portions of integrated lights 16. It is also contemplated that light emitter 36 may be active in that it may extend as an interface between adjacent lights 16 receiving electrical power and coupling it between the adjacent lights 16 and contain some LEDs that emit light outward from cap 36, so as to make linear light array 54 appear to emit light along the areas that would not normally emit light due to the nature of the construct of integrated lights 16. This advantageously will then have a continuous light lines along the surface of a vehicle that is passing through inspection system 10. Cap 36 may be integral with one end of a light 16, or may be coupled thereto by way of a releasable coupling or by a chemical bonding, such as the use of a glue.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An inspection lighting system, comprising:
   a first frame structure; and
   a plurality of linear light arrays coupled to the first frame structure, a portion of the frame structure being generally perpendicular to the linear light arrays, the linear light arrays being generally parallel to each other, each linear light array including:
      a plurality of integrated lights arranged end-to-end, each of the integrated lights having at least one T-slot along at least a portion of a length of the integrated light; and
      at least one generally linear bracket coupling adjacent ones of the integrated lights together using the T-slots in the adjacent integrated lights.

2. The inspection lighting system of claim 1, wherein the bracket only couples adjacent integrated lights together and is not coupled to the first frame.

3. The inspection lighting system of claim 1, further comprising a second frame structure arranged substantially parallel to the first frame structure, the second frame structure also having a plurality of linear light arrays coupled thereto.

4. The inspection lighting system of claim 3, wherein the linear light arrays coupled to the first frame structure generally emanate light toward the second frame structure.

5. The inspection lighting system of claim 3, wherein the plurality of linear light arrays coupled to the first frame structure include a first linear light array, the plurality of linear light arrays coupled to the second frame structure include a second linear light array.

6. The inspection lighting system of claim 5, wherein the first linear light array and the second linear light array are arranged opposite each other.

7. The inspection lighting system of claim 6, further comprising a third linear light array that is coupled to both the first linear light array and the second linear light array.

8. The inspection lighting system of claim 7, further comprising an angular bracket coupling an end of the first linear light array to an end of the third linear light array, the angular bracket using the T-shaped slots of one of the integrated lights of the first linear light array.

9. The inspection lighting system of claim 8, wherein the third linear light array is only coupled to the first linear light array and the second linear light array.

10. The inspection lighting system of claim 3, further comprising a plurality of top linear light arrays, each of the top linear light arrays being coupled to one of the linear light arrays coupled to the first frame structure and to one of the linear light arrays coupled to the second frame structure.

11. An inspection lighting system, comprising:
a first frame structure; and
a plurality of linear light arrays coupled to the first frame structure, a portion of the frame structure being generally perpendicular to the linear light arrays, the linear light arrays being generally parallel to each other, each linear light array including:
a plurality of integrated lights with adjacent ones of the plurality of integrated lights being coupled end-to-end defining a joint; and
at least one light emitter coupled at the joint, the light emitter covering a non-light emitting portion of each of the adjacent integrated lights, the light emitter transmitting light outward over the non-light emitting portion.

12. The inspection lighting system of claim 11, wherein the light emitter receives light from at least one of the adjacent integrated lights.

13. The inspection lighting system of claim 11, further comprising a second frame structure arranged substantially parallel to the first frame structure, the second frame structure also having a plurality of linear light arrays coupled thereto, the linear light arrays coupled to the first frame structure being substantially similar to the linear light arrays coupled to the second frame structure.

14. The inspection lighting system of claim 13, wherein the linear light arrays coupled to the first frame structure generally emanate light toward the second frame structure.

15. The inspection lighting system of claim 13, wherein the plurality of linear light arrays coupled to the first frame structure include a first linear light array, the plurality of linear light arrays coupled to the second frame structure include a second linear light array.

16. The inspection lighting system of claim 15, wherein the first linear light array and the second linear light array are arranged opposite each other.

17. The inspection lighting system of claim 16, further comprising a third linear light array that is coupled to both the first linear light array and the second linear light array.

18. The inspection lighting system of claim 17, further comprising an angular bracket coupling an end of the first linear light array to an end of the third linear light array, the angular bracket using T-shaped slots of the integrated lights.

19. The inspection lighting system of claim 18, wherein the third linear light array is only coupled to the first linear light array and the second linear light array.

20. The inspection lighting system of claim 13, further comprising a plurality of top linear light arrays, each of the top linear light arrays being coupled to one of the linear light arrays coupled to the first frame structure and to one of the linear light arrays coupled to the second frame structure.

* * * * *